United States Patent
Kiriu et al.

(10) Patent No.: US 10,703,726 B2
(45) Date of Patent: Jul. 7, 2020

(54) METHOD FOR PRODUCING RADIOPHARMACEUTICAL COMPOSITION

(71) Applicants: Nihon Medi-Physics Co., Ltd., Tokyo (JP); National University Corporation Hokkaido University, Sapporo-shi, Hokkaido (JP)

(72) Inventors: Masato Kiriu, Tokyo (JP); Soichi Nakamura, Tokyo (JP); Yuji Kuge, Sapporo (JP); Norifumi Abo, Sapporo (JP)

(73) Assignees: NIHON MEDI-PHYSICS CO., LTD., Koto-Ku, Tokyo (JP); NATIONAL UNIVERSITY CORPORATION HOKKAIDO UNIVERSITY, Sapporo-Shi, Hokkaido (JP)

( * ) Notice: Subject to any disclaimer, the term of this patent is extended or adjusted under 35 U.S.C. 154(b) by 0 days.

(21) Appl. No.: 16/288,855

(22) Filed: Feb. 28, 2019

(65) Prior Publication Data
US 2019/0276411 A1    Sep. 12, 2019

(30) Foreign Application Priority Data
Mar. 7, 2018  (JP) .................................. 2018-040919

(51) Int. Cl.
| | | |
|---|---|---|
| *C07D 233/91* | (2006.01) | |
| *A61K 51/04* | (2006.01) | |
| *C07D 233/94* | (2006.01) | |
| *C07B 59/00* | (2006.01) | |

(52) U.S. Cl.
CPC ........ *C07D 233/91* (2013.01); *A61K 51/0453* (2013.01); *C07B 59/002* (2013.01); *C07D 233/94* (2013.01); *C07B 2200/05* (2013.01)

(58) Field of Classification Search
CPC .. C07D 233/91; C07D 233/94; C07B 59/002; A61K 51/0453
See application file for complete search history.

(56) References Cited

U.S. PATENT DOCUMENTS

| | | | |
|---|---|---|---|
| 2014/0364620 A1 | 12/2014 | Nakata et al. | |
| 2017/0066748 A1* | 3/2017 | Toyama | C07D 405/06 |

FOREIGN PATENT DOCUMENTS

| | | |
|---|---|---|
| JP | 2015504443 A | 2/2015 |
| JP | 2015081242 A | 4/2015 |
| WO | 2013042668 A1 | 3/2013 |
| WO | 2013079578 A1 | 6/2013 |

OTHER PUBLICATIONS

Machine English Translation of JP2015081242, published on Apr. 27, 2015.*
Knott et al.: "Simplified and automatic one-pot synthesis of 16α-[18F]fluoroestradiol without high-performance liquid chromatography purification," Journal of Labelled Compounds and Radiopharmaceuticals, vol. 54, No. 12, Oct. 1, 2011, pp. 749-753, XP055592833 (6 pages).
Extended Search Report issued by the European Patent Office in corresponding European Patent Application No. 19160258.0-1110 dated Jun. 11, 2019 (9 pages).

* cited by examiner

*Primary Examiner* — Joseph R Kosack
(74) *Attorney, Agent, or Firm* — Buchanan Ingersoll & Rooney PC

(57) ABSTRACT

A simple method for producing a clinically applicable radiopharmaceutical composition containing 1-(2,2-dihydroxymethyl-3-[$^{18}$F]fluoropropyl)-2-nitroimidazole ([$^{18}$F]DiFA) or a salt thereof as an active ingredient, is provided which includes a synthesis step of obtaining a crude product of [$^{18}$F]DiFA from a labeling precursor compound for [$^{18}$F]DiFA; and a purification step of purifying the crude product, in which the purification step includes purifying [$^{18}$F]DiFA using two or more different types of reverse phase solid phase extraction cartridges.

5 Claims, No Drawings

METHOD FOR PRODUCING RADIOPHARMACEUTICAL COMPOSITION

BACKGROUND

Technical Field

The present invention relates to a method for producing a radiopharmaceutical composition containing a radioactive fluorine-labeled compound as an active ingredient.

Related Art

As an attempt to detect a hypoxic region in vivo, single photon emission tomography (SPECT) and positron emission tomography (PET) using radioactive compounds labeled with radionuclides have been performed.

1-(2,2-dihydroxymethyl-3-[$^{18}$F]fluoropropyl)-2-nitroimidazole (hereinafter also abbreviated as "[$^{18}$F]DiFA") has been reported by the present applicants as one of the compounds with which a hypoxic region in a living body can be quantitatively evaluated with high accuracy (WO 2013/042668 A).

As a method capable of producing [$^{18}$F]DiFA having a clinically applicable purity, the following method is described in JP 2015-81242 A. That is, a [$^{18}$F] fluorine labeling reaction is performed using 2,2-dimethyl-5-[(2-nitro-1H-imidazol-1-yl)methyl]-5-(p-toluenesulfonyloxymethyl)-1,3-dioxane as a labeling precursor compound, and then an acetonide protecting group is removed with hydrochloric acid. After completion of the reaction, tosylic acid and analogous substances are eluted by chromatography using octadecylsilylated silica gel as a stationary phase and a mixture of water and ethanol as an eluent, and then [$^{18}$F]DiFA is eluted to obtain highly purified [$^{18}$F]DiFA.

JP 2015-504443 A does not disclose anything about [$^{18}$F]DiFA but describes purification of a $^{18}$F-labeled compound using a solid phase extraction column.

SUMMARY

However, the method described in JP 2015-81242 A requires a large-scale HPLC apparatus, and therefore has a problem in terms of handling.

In addition, [$^{18}$F]DiFA eluted from the HPLC apparatus contains a large amount of eluent. Therefore, a concentration step is required for obtaining a formulation, and production time is long. In addition, according to the present inventors' finding, it has been clarified that radiochemical foreign matters are generated by heating for concentration in a short time.

The present invention has been achieved in view of the above circumstances. An object of the present invention is to provide a technique for producing a clinically applicable radioactive fluorine-labeled body of 1-(2,2-dihydroxymethyl-3-[$^{18}$F]fluoropropyl)-2-nitroimidazole ([$^{18}$F]DiFA) by a simpler method.

The present inventors have found that impurity-removed [$^{18}$F]DiFA can be obtained by a solid phase extraction method using two or more different types of reverse phase solid phase extraction cartridges instead of a conventional HPLC method, and have completed the present invention.

That is, an embodiment of the present invention provides a method for producing a radiopharmaceutical composition containing a radioactive fluorine-labeled compound represented by the following general formula (1) or a salt thereof as an active ingredient, including: a synthesis step of obtaining a crude product of the radioactive fluorine-labeled compound from a labeling precursor compound represented by the following formula (2); and a purification step of purifying the radioactive fluorine-labeled compound, in which the purification step includes purifying the radioactive fluorine-labeled compound using two or more different types of reverse phase solid phase extraction cartridges.

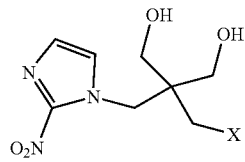

(1)

wherein X represents a radioactive fluorine atom.

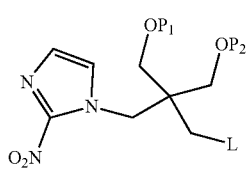

(2)

wherein $P_1$ and $P_2$ independently or together represent a hydroxy group-protecting group, and L represents a leaving group.

Here, in the present invention, "radioactive fluorine" is a radioactive isotope of fluorine, and specifically, fluorine-18 is used. By using fluorine-18, a biodistribution of [$^{18}$F]DiFA can be imaged by positron emission tomography (PET).

According to an embodiment of the present invention, purification is performed using two or more different types of reverse phase solid phase extraction cartridges, and therefore [$^{18}$F]DiFA from which impurities have been removed can be easily obtained as compared with purification by a conventional HPLC method.

DETAILED DESCRIPTION

An embodiment of the present invention relates to a method for producing a radiopharmaceutical composition containing 1-(2,2-dihydroxymethyl-3-[$^{18}$F]fluoropropyl)-2-nitroimidazole ([$^{18}$F]DiFA) represented by the above general formula (1) or a salt thereof as an active ingredient.

In the present invention, the "radiopharmaceutical composition" can be defined as a formulation containing [$^{18}$F]DiFA in a form suitable for administration into a living body. The radiopharmaceutical composition is preferably administered parenterally, that is, by injection, and is more preferably in a form of an aqueous solution.

[$^{18}$F]DiFA may form a salt. Specific examples of the salt include a salt with an inorganic acid such as hydrochloric acid, hydrobromic acid, hydroiodic acid, sulfuric acid, nitric acid, or phosphoric acid; and a salt with an organic acid such as formic acid, acetic acid, trifluoroacetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid, or glutamic acid.

In the present invention, the phrase "containing . . . as an active ingredient" only requires that [$^{18}$F]DiFA is contained to a degree that efficacy of [$^{18}$F]DiFA can be exerted, and specifically that [$^{18}$F]DiFA is contained in a predetermined range of radioactivity concentration. For example, the radioactivity concentration of [$^{18}$F]DiFA at the time of use is preferably 10 to 1000 MBq/mL, and more preferably 50 to 500 MBq/mL.

The producing method according to an embodiment of the present invention includes a synthesis step of obtaining a crude product of [$^{18}$F]DiFA from a compound represented by the above formula (2), for example, 2,2-dimethyl-5-[(2-nitro-1H-imidazol-1-yl)methyl]-5-(p-toluenesulfonyloxymethyl)-1,3-dioxane (labeling precursor compound), and a purification step of purifying [$^{18}$F]DiFA. In the purification step, purification is performed using two or more different types of reverse phase solid phase extraction cartridges. In the purification step according to an embodiment of the present invention, it is not necessary to perform purification by a high performance liquid chromatography (HPLC) method.

Synthesis Step

Specifically, the synthesis step includes the following [$^{18}$F] fluorination step and deprotection step.

[$^{18}$F] Fluorination Step: A labeling precursor is allowed to react with [$^{18}$F] fluoride ion to obtain a protected [$^{18}$F]DiFA.

Deprotection step: Hydroxy group-protecting group is removed from the protected [$^{18}$F]DiFA to obtain a crude product of [$^{18}$F]DiFA.

A labeling precursor compound can be obtained by providing 2-bromomethyl-2-hydroxymethyl-1,3-propanediol as a starting material, protecting the two hydroxy groups of the diol, and then introducing 2-nitroimidazole and a leaving group thereinto. Specifically, for example, the labeling precursor compound can be synthesized by a method described in WO 2013/042668 A.

In the above formula (2), $P_1$ and $P_2$ represent hydroxy group-protecting groups which may be the same as or different from each other, or $P_1$ and $P_2$ together represent a diol-protecting group. As the hydroxy group-protecting group and the diol-protecting group, those described in Greene's Protective Groups in Organic Synthesis (John Wiley & Sons Inc; 5th edition) can be used. In a case where $P_1$ and $P_2$ independently represent the same hydroxy group-protecting group or hydroxy group-protecting groups different from each other, $P_1$ and $P_2$ can be preferably selected from the group consisting of a trityl group, a monomethoxytrityl group, a dimethoxytrityl group, a trimethoxytrityl group, a methoxymethyl group, an 1-ethoxyethyl group, a methoxyethoxymethyl group, a benzyl group, a p-methoxybenzyl group, a 2-tetrahydropyranyl group, a trimethylsilyl group, a triethylsilyl group, a t-butyldimethylsilyl group, a t-butyldiphenylsilyl group, an acetyl group, a propanoyl group, a pivaloyl group, a palmitoyl group, a dimethylaminomethylcarbonyl group, an alanyl group, a 2,2,2-trichloroethoxycarbonyl group, a benzoyl group, and an allyloxycarbonyl group. In the above formula (2), in a case where $P_1$ and $P_2$ together represent a diol-protecting group, for example, $P_1$ and $P_2$ together represent a methylene group [—$CH_2$—], a 1-methylethane-1,1-diyl group [—$C(CH_3)_2$—], an ethane-1,1-diyl group [—CH($CH_3$)—], or a 1-phenylmethane-1,1-diyl group [—CHPh] so that a 1,3-dioxane ring is formed. Among these groups, $P_1$ and $P_2$ preferably represent an acetonide group.

In the formula (2), L is not particularly limited as long as being a functional group capable of causing a nucleophilic substitution reaction, and represents a non-radioactive halogen atom, a trialkylammonium having 3 to 12 carbon atoms, a linear or branched alkylsulfonyloxy group having 1 to 10 carbon atoms, a linear or branched halogenoalkylsulfonyloxy group having 1 to 10 carbon atoms, a substituted or unsubstituted arylsulfonyloxy group, or a dialkylsulfonyloxy group having 2 to 8 carbon atoms. L is preferably selected from the group consisting of chlorine atom (Cl), bromine atom (Br), iodine atom (I), tosyl group (OTs), mesyl group (OMs), and triflate group (OTf), and is more preferably triflate group (OTs).

[$^{18}$F] fluoride ion can be prepared by any known methods, and examples thereof include the following method. First, [$^{18}$F] fluoride ion is produced from [$^{18}$O] water by a cyclotron and collected in a carbonate type anion exchange resin. Subsequently, a potassium carbonate aqueous solution is allowed to pass through the anion exchange resin to elute the [$^{18}$F] fluoride ion. This makes it possible to obtain the [$^{18}$F] fluoride ion as a [$^{18}$F] potassium fluoride aqueous solution. In order to improve [$^{18}$F] fluorination labeling efficiency, the obtained [$^{18}$F] fluoride ion is preferably activated by the following additional operation. That is, Kryptofix 222 (trade name: 1,10-diaza-4,7,13,16,21,24-hexaoxabicyclo [8.8.8] hexacosane) is added to the eluate of the [$^{18}$F] fluoride ion, and the resulting mixture is subjected to azeotrope with acetonitrile. As a result, the [$^{18}$F] fluoride ion can be obtained as a mixture of potassium carbonate and Kryptofix 222. Note that Kryptofix 222 may be allowed to pass through the anion exchange resin together with the potassium carbonate aqueous solution. Alternatively, [$^{18}$F] fluoride ion may be collected in a bicarbonate type anion exchange resin, a tetraammonium bicarbonate aqueous solution may be allowed to pass therethrough to elute the [$^{18}$F] fluoride ion, and the resulting eluate may be subjected to azeotrope with acetonitrile.

The [$^{18}$F] fluoride ion thus obtained is mixed with the labeling precursor compound to perform a [$^{18}$F] fluorination reaction. The reaction is preferably performed in a suitable solvent such as an aprotic solvent such as acetonitrile, N,N-dimethylformamide, or dimethylsulfoxide at a temperature of 20 to 120° C. After completion of the reaction, the solvent is evaporated to obtain a protected [$^{18}$F]DiFA.

The deprotection step is not particularly limited as long as being performed under conditions in which the hydroxy group-protecting group can be removed, and in general, hydrolysis is performed using an acid or a base. However, in a case where an acetonide group is used as a protecting group, acid hydrolysis is preferably performed. In this case, an acid that can be used is not particularly limited, but is preferably hydrochloric acid. As for reaction conditions, the reaction is preferably performed at a temperature higher than room temperature, for example, at a temperature of 50 to 100° C. from a viewpoint of being able to shorten reaction time.

After deprotection of the acetonide protecting group is completed, the resulting solution is diluted with water, then t a crude product of [$^{18}$F]DiFA can be obtained. Neutralization using a base such as sodium acetate which has been conventionally performed may be performed, but does not have to be performed. Here, the "crude product" only needs to be unpurified [$^{18}$F]DiFA and contains at least one inorganic compound or organic compound other than [$^{18}$F]DiFA as an impurity. These impurities are derived from a reaction reagent, a reaction by-product, and others used in the synthesis step. This crude product is preferably a solution of [$^{18}$F]DiFA, and more preferably an aqueous solution of [$^{18}$F]DiFA.

Examples of the organic compound other than [$^{18}$F]DiFA include a labeling precursor represented by the above formula (2), 1-(2,2-dihydroxymethyl-3-hydroxypropyl)-2-nitroimidazole (hereinafter also referred to as "the OH form") represented by the following formula (3), the OH form that is still protected, 2-chloromethyl-2-hydroxymethyl-3-hydroxypropyl-2-nitroimidazole (hereinafter also referred to as "the Cl form") represented by the following formula (4), and the above-described protected [$^{18}$F]DiFA.

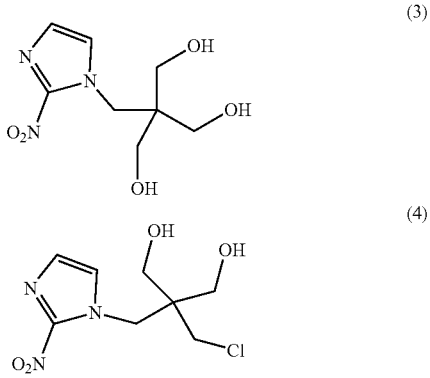

Purification Step

In the purification step, [$^{18}$F]DiFA obtained as a crude product in the synthesis step is purified. Specifically, by performing purification by a solid phase extraction method using two or more different types of reverse phase solid phase extraction cartridges, [$^{18}$F]DiFA is separated from one or more of the above-described impurities.

In the present invention, the reverse phase solid phase extraction cartridge refers to a cartridge that is filled with a silica-based or polymer-based nonionic adsorbent having low polarity as a stationary phase, and has a property of adsorbing a substance with higher hydrophobicity more strongly. Specific examples of the polymer-based adsorbent include a poly(divinylbenzene-co-N-vinylpyrrolidone) polymer and a styrene-divinylbenzene polymer having an N-vinylpyrrolidone functional group. Specific examples of the silica-based adsorbent include silica gel chemically modified with a butyl group (C4), an octyl group (C8), an octadecyl group (C18), or a triacontyl group (C30).

In the purification step according to an embodiment of the present invention, two or more different types of reverse phase solid phase extraction cartridges are used to purify [$^{18}$F]DiFA by the solid phase extraction method. Solid phase extraction cartridges and mobile phases only have to be selected such that impurities are eluted in the order of lower hydrophobicity to recover [$^{18}$F]DiFA. A combination of a polymer-based reverse phase solid phase extraction cartridge and a silica-based reverse phase solid phase extraction cartridge is preferable, and a combination of a reverse phase solid phase extraction cartridge using a poly(divinylbenzene-co-N-vinylpyrrolidone) polymer as an adsorbent and a reverse phase solid phase extraction cartridge using octadecylsilylated silica gel as an adsorbent is more preferable.

In the purification step according to an embodiment of the present invention, it is preferable that impurities (for example, the OH form) with lower hydrophobicity than [$^{18}$F]DiFA are removed using a first reverse phase solid phase extraction cartridge (the first purification step), and impurities (for example, the Cl form, the labeling precursor, or the protected [$^{18}$F]DiFA) with higher hydrophobicity than [$^{18}$F]DiFA are removed using a second reverse phase solid phase extraction cartridge (the second purification step). As the first reverse phase solid phase extraction cartridge, a reverse phase solid phase extraction cartridge filled with a polymer-based adsorbent as a stationary phase is preferable, and a reverse phase solid phase extraction cartridge using a poly(divinylbenzene-co-N-vinylpyrrolidone) polymer as an adsorbent is more preferable. As the second reverse phase solid phase extraction cartridge, a reverse phase solid phase extraction cartridge filled with a silica-based adsorbent as a stationary phase is preferable, and a reverse phase solid phase extraction cartridge using octadecylsilylated silica gel as an adsorbent is more preferable. The order for performing the first purification step and the second purification step is not particularly limited. However, the second purification step is preferably performed after the first purification step, and the second purification step is preferably performed after the first purification step in a successive manner. The phrase "in a successive manner" in the present invention means that no other purification step is interposed between two successive purification steps.

Examples of the reverse phase solid phase extraction cartridge using a poly(divinylbenzene-co-N-vinylpyrrolidone) polymer as an adsorbent, used in the present invention, include Oasis HLB Plus Short Cartridge 225 mg and Oasis HLB Plus Light Cartridge 30 mg manufactured and sold by Waters Corporation, InertSep SlimJ PLS-2 230 mg manufactured and sold by GL Sciences Inc., and NEXUS, Bond Elut Jr 200 mg manufactured and sold by Agilent Technologies Japan, Ltd. Examples of the reverse phase solid phase extraction cartridge using octadecylsilylated silica gel as an adsorbent include Sep-pak C18 Plus Short Cartridge 360 mg and Sep-pak tC18 Plus Short Cartridge 360 mg manufactured and sold by Waters Corporation, InertSep Slim C18 400 mg, InertSep SlimJ C18 400 mg, Bond Elut C18, and Bond Elut Jr 500 mg manufactured and sold by GL Sciences Inc., and Bond Elut C18 OH and Bond Elut Jr 500 mg manufactured and sold by Agilent Technologies Japan, Ltd.

The first purification step can include, for example, a step of injecting a crude product into a reverse phase solid phase extraction cartridge to allow [$^{18}$F]DiFA to be adsorbed on the reverse phase solid phase extraction cartridge, a step of allowing a washing liquid to pass through the reverse phase solid phase extraction cartridge on which [$^{18}$F]DiFA has been adsorbed to wash the reverse phase solid phase extraction cartridge, and a step of allowing an eluent to pass through the reverse phase solid phase extraction cartridge to elute [$^{18}$F]DiFA from the reverse phase solid phase extraction cartridge.

The washing liquid used in the first purification step may be any liquid as long as not eluting [$^{18}$F]DiFA but eluting a substance having a higher polarity than [$^{18}$F]DiFA, and includes water, saline, or an ethanol aqueous solution. The ethanol aqueous solution as a washing liquid has an ethanol concentration of preferably 3 to 15% by volume, more preferably 4 to 10% by volume. In the first purification step, the reverse phase solid phase extraction cartridge may be washed once or a plurality of times using the same washing liquid or may be washed a plurality of times using different washing liquids.

The eluent used in the first purification step is not particularly limited as long as being able to elute [$^{18}$F]DiFA that has been adsorbed on the reverse phase solid phase extraction cartridge, but is preferably an ethanol aqueous solution. The ethanol concentration of the ethanol aqueous solution as an eluent is preferably different from that of a washing liquid, and more preferably higher than that of the washing liquid. Specifically, an ethanol aqueous solution containing 15% by volume or more ethanol is preferable, and an aqueous ethanol solution containing 18% by volume or more ethanol is particularly preferable.

The second purification step is performed, for example, by allowing the eluate of [$^{18}$F]DiFA obtained in the first purification step to pass through a reverse phase solid phase extraction cartridge. Here, impurities having higher hydrophobicity than [$^{18}$F]DiFA are collected in the reverse phase solid phase extraction cartridge. Incidentally, prior to allowing the eluate of [$^{18}$F]DiFA obtained in the first purification step to pass through the reverse phase solid phase extraction cartridge, water, physiological saline, ethanol, or the like may be added to the eluate of [$^{18}$F]DiFA to adjust the polarity of the solvent, or a stabilizer such as ascorbic acid or mannitol described in a preparation step described later may be added thereto.

The purification step according to an embodiment of the present invention may further include a third purification step of removing ionic impurities using an ion exchange solid phase extraction cartridge. The third purification step can be performed, for example, by allowing a liquid to pass through an ion exchange solid phase extraction cartridge. In a case where deprotection is performed by acid hydrolysis using hydrochloric acid, chloride ion can be thereby removed.

In the purification step according to an embodiment of the present invention, the first purification step, the second purification step, and the third purification step may be performed in any order, but the third purification step is preferably performed as the first or last step, and is more preferably performed as the first step. In addition, the second purification step is preferably performed after the first purification step. In the most preferable embodiment, the first purification step is performed in a successive manner after the third purification step, and then the second purification step is performed in a successive manner after the first purification step.

Preparation Step

In the preparation step, radioactivity concentration of [$^{18}$F]DiFA is adjusted by adding injection water or physiological saline directly to the [$^{18}$F]DiFA solution obtained in the purification step without concentrating the [$^{18}$F]DiFA solution. Thereafter, sterile filtration is performed with a membrane filter to obtain [$^{18}$F]DiFA as an injection.

The preparation step may further include a stabilization step of mixing [$^{18}$F]DiFA with a stabilizer such as ascorbic acid or mannitol. This makes it possible to suppress radiolysis of [$^{18}$F]DiFA and to obtain a radiopharmaceutical composition with reduced radioactive impurities even during use. This stabilization step may be performed by adding a stabilizer to a solution containing [$^{18}$F]DiFA when the solution containing [$^{18}$F]DiFA is injected into a solid phase extraction cartridge in the second or third purification step, or by adding a stabilizer to an eluent in the step of eluting [$^{18}$F]DiFA in the first purification step.

Each of the ascorbic acid and mannitol as a stabilizer preferably has a concentration in a range of 5 to 70 µmol/mL in a radiopharmaceutical composition obtained by the producing method according to an embodiment of the present invention. The concentration of ascorbic acid is more preferably in a range of 50 to 70 µmol/mL. The concentration of mannitol is more preferably in a range of 5 to 15 µmol/mL.

Radiopharmaceutical Composition

By using the above producing method, a radiopharmaceutical composition containing [$^{18}$F]DiFA as an active ingredient can be provided.

Such a composition may contain an additional ingredient such as a pH adjusting agent, a pharmaceutically acceptable solubilizer, a stabilizer, or an antioxidant appropriately. For example, the radiopharmaceutical composition may contain ascorbic acid or mannitol as a stabilizer. The concentrations of these compounds can be preferably in a range that can be adopted in the above-described preparation step.

In the method according to an embodiment of the present invention, impurities are removed to a clinically applicable degree. Therefore, the radiopharmaceutical composition according to an embodiment of the present invention is highly safe and can be administered to a human body. After administration, by detecting a radiation emitted from an inside of a body with a PET device, a hypoxic region in the body can be noninvasively detected so that diagnosis of a disease such as cancer or decision of a treatment policy can be made.

EXAMPLES

Hereinafter, the present invention will be described in more detail by describing Examples, but the present invention is not limited to these contents.

Hereinafter, 2,2-dimethyl-5-[(2-nitro-1H-imidazol-1-yl)methyl]-5-(p-toluenesulfonyloxymethyl)-1,3-dioxane (a compound in which $P_1$ and $P_2$ together form an acetonide group and L represents a tosyl group in the formula (1), i.e., the tosylated compound) used in Examples was synthesized according to a method of Example 1 of WO 2013/042668 A. In addition, 1-(2,2-dihydroxymethyl-3-fluoropropyl)-2-nitroimidazole (a compound obtained by replacing fluorine-18 in [$^{18}$F]DiFA with fluorine-19, hereinafter also referred to as "the DiFA standard") was synthesized according to a method of Example 2 of WO 2013/042668 A.

Examples 1 to 4: Production of [$^{18}$F]DiFA Formulation

[$^{18}$F] fluoride ion-containing [$^{18}$O] water (see Table 2 for the amount of radioactivity) taken out from a cyclotron (product name: HM-18, manufactured by Sumitomo Heavy Industries, Ltd., irradiation condition: 25 µA, 20 min) was allowed to pass through an anion exchange cartridge (Sep-Pak (registered trademark) Accell Plus QMA carbonate Plus Light (trade name), manufactured by Nihon Waters K.K.) to adsorb and collect [$^{18}$F] fluoride ion. Subsequently, a potassium carbonate aqueous solution (0.2 mL, see the column of $K_2CO_3$ in Table 1 for the amount of potassium carbonate used) and an acetonitrile solution of Kryptofix 222 (trade name, manufactured by Merck) (0.7 mL, see the column of K222 in Table 1 for the amount of Kryptofix 222 used) were allowed to pass through the above anion exchange cartridge to elute [$^{18}$F] fluoride ion. The resulting eluate was heated under nitrogen flow at 110° C. for 7.5 minutes to evaporate water. Thereafter, acetonitrile (0.3 mL×2) was added thereto, and the resulting mixture was subjected to azeotrope, dried, and solidified. An acetonitrile solution (0.9 mL) in which the tosylated compound (5 mg, 11.4 µmol) was dissolved was added thereto. The resulting mixture was heated at 110° C. for the labeling time shown in Table 1. The resulting solution was heated at 110° C. for three minutes to concentrate the solution. Thereafter, 1 mol/L hydrochloric acid (1.0 mL) was added thereto, and the resulting mixture was heated at 110° C. for three minutes. After completion of the reaction, the resulting solution was diluted with injection water (14 mL). The diluted solution was allowed to pass through an anion exchange cartridge (Sep-Pak (registered trademark) Accell Plus QMA carbonate Plus Light (trade name), manufactured by Nihon Waters K.K.) and a reverse phase solid phase extraction cartridge (Oasis HLB Plus Short Cartridge 225 mg, manufactured by Waters Corporation) (hereinafter referred to as "the HLB cartridge") using a poly(divinylbenzene-co-N-vinylpyrrolidone) polymer as an adsorbent. Subsequently, injection water (10 mL) was allowed to pass through the HLB cartridge. Thereafter, the HLB cartridge was washed with a washing liquid shown in Table 1.

Thereafter, elution was performed with physiological saline (5 mL) containing 20% by volume ethanol, and the resulting eluate was allowed to pass through a reverse phase solid phase extraction cartridge (Sep-pak C18 Plus Short Cartridge 360 mg, manufactured by Waters Corporation) using octadecylsilylated silica gel as an adsorbent. Furthermore, physiological saline (10 mL) was allowed to pass through the HLB cartridge, and the obtained eluate was allowed to pass through a reverse phase solid phase extraction cartridge (Sep-Pak (registered trademark) C18 (trade name) manufactured by Nihon Waters K.K.) using octadecylsilylated silica gel as an adsorbent. The resulting eluates were combined and aseptically filtered to obtain a [$^{18}$F]DiFA injection liquid (see the column of radioactivity recovered shown in Table 2 for the amount of radioactivity).

Results are shown in Table 2. Note that analysis conditions of TLC and analysis conditions of HPLC were as follows. The radiochemical yield was calculated as a percentage of the amount of radioactivity (without attenuation correction) of the [$^{18}$F]DiFA injection liquid relative to the amount of radioactivity at the time of starting synthesis. In addition, the concentration of analogous substances was calculated using an HPLC analytical value of the DiFA standard.

<TLC Analysis Conditions>
Carrier: silica gel 60F$_{254}$
Mobile phase: ethyl acetate/methanol/triethylamine=5:1:0.5 (volume ratio)
Development distance: 10 cm
<HPLC Analysis Conditions>
Detector: ultraviolet-visible absorption detector (325 nm)
Column: YMC TriartC18 (4.6 mm i.d.×150 mm, 5 μm)
Column temperature: room temperature (constant temperature around 25° C.)
Flow rate: 1 mL/min Mobile phase: 50 mM ammonium carbonate aqueous solution/acetonitrile=9:1 (volume ratio)
Injection amount: 10 μL

TABLE 1

| Entry | K222 | K$_2$CO$_3$ | Labeling time | Washing liquid |
|---|---|---|---|---|
| Example 1 | 14 mg | 2.0 mg | 10 minutes | 5% by volume ethanol (10 mL) |
| Example 2 | 14 mg | 2.0 mg | 10 minutes | 5% by volume ethanol (15 mL) |
| Example 3 | 7 mg | 1.0 mg | 10 minutes | 5% by volume ethanol (10 mL) |
| Example 4 | 14 mg | 2.0 mg | 5 minutes | 5% by volume ethanol (10 mL) |

TABLE 2

| Entry | Radioactivity charged (MBq) | Radioactivity recovered (MBq) | Production time (min) | Radiochemical yield (%) | Radiochemical purity[a] | Total amount of analogous substances (μg/mL)[b] |
|---|---|---|---|---|---|---|
| Example 1 | 921 | 320 | 45 | 34.7 | 100% | 12.74 |
| Example 2 | 534 | 140.7 | 46 | 26.3 | 100% | 7.43 |
| Example 3 | 504 | 146.3 | 48 | 29.0 | 100% | 7.99 |
| Example 4 | 581 | 207 | 39 | 35.6 | 100% | 11.92 |

[a]Evaluated with TLC
[b]Evaluated with HPLC

The production result according to the method of Example 4 of JP 2015-81242 A was that the radiochemical yield was 30% on average, the radiochemical purity was 96 to 98%, the production time was about 80 minutes, and the total amount of analogous substances was about 0.5 μg/mL at the amount of charged radioactivity of about 20 GBq. In contrast, by the methods of Examples 1 to 4, the radiochemical yield was nearly equal to the above result, but the radiochemical purity was improved, and the production time was shortened to 39 to 48 minutes. Furthermore, the amounts of analogous substances in Examples 1 to 4 correspond to an intake of 50 μg or less at maximum, considering that the maximum of the clinically administered liquid amount is 3 mL. This amount is clinically administrable according to the "guidance on implementation of microdose clinical trial (Drug Deliberation Examination No. 0603001, Jun. 3, 2008)".

From the above, it has been suggested that it is possible to obtain a clinically applicable [$^{18}$F]DiFA formulation easily with high yield by the method according to an embodiment of the present invention.

This application claims the priority based on Japanese Patent Application No. 2018-40919 filed on Mar. 7, 2018, the disclosure of which is incorporated herein by reference in its entirety.

What is claimed is:

1. A method for producing a radiopharmaceutical composition containing a radioactive fluorine-labeled compound represented by the following general formula (1) or a salt thereof as an active ingredient, comprising:
a synthesis step of obtaining a crude product of the radioactive fluorine-labeled compound from a labeling precursor compound represented by the following formula (2); and
purification steps of purifying the radioactive fluorine-labeled compound, wherein
the purification steps include:
a first purification step using a first reverse phase solid phase extraction cartridge filled with a poly(divinylbenzene-co-N-vinylpyrrolidone) polymer; and
a second purification step using a second reverse phase solid phase extraction cartridge filled with octadecylsilylated silica gel,
wherein the first purification step includes:
adsorbing the radioactive fluorine-labeled compound on the first reverse phase solid phase extraction cartridge;
washing the first reverse phase solid phase extraction cartridge on which the radioactive fluorine-labeled compound has been adsorbed with a washing liquid; and
eluting the radioactive fluorine-labeled compound from the first reverse phase solid phase extraction cartridge by allowing an eluent to pass through the first reverse phase solid phase extraction cartridge, wherein the washing liquid is an ethanol aqueous solution containing 4 to 10% by volume ethanol, and the eluent is an ethanol aqueous solution containing 15% by volume or more ethanol,

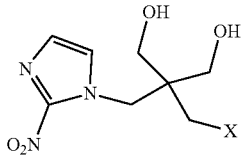

(1)

wherein X represents a radioactive fluorine atom;

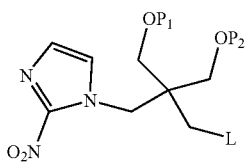

(2)

wherein $P_1$ and $P_2$ independently or together represent a hydroxy group-protecting group, and L represents a tosyl group.

2. The method for producing a radiopharmaceutical composition according to claim 1, wherein
the eluent is an ethanol aqueous solution containing 18% by volume or more ethanol.

3. The method for producing a radiopharmaceutical composition according to claim 1, wherein the second purification step is performed by allowing the eluate of the radioactive fluorine-labeled compound obtained in the first purification step to pass through the second reverse phase solid phase extraction cartridge.

4. The method for producing a radiopharmaceutical composition according to claim 1, wherein the purification steps further includes a third purification step of removing ionic impurities using an ion exchange solid phase extraction cartridge.

5. The method for producing a radiopharmaceutical composition according to claim 1, wherein the purification steps are free from purification by a high performance liquid chromatography method.

* * * * *